(12) United States Patent
Fine

(10) Patent No.: US 12,123,868 B2
(45) Date of Patent: Oct. 22, 2024

(54) INDICATOR-BASED ANALYSIS OF A SAMPLE

(71) Applicant: Alentic Microscience Inc., Halifax (CA)

(72) Inventor: Alan Marc Fine, Prospect (CA)

(73) Assignee: Alentic Microscience Inc., Halifax (CA)

( * ) Notice: Subject to any disclaimer, the term of this patent is extended or adjusted under 35 U.S.C. 154(b) by 0 days.

(21) Appl. No.: 18/167,557

(22) Filed: Feb. 10, 2023

(65) Prior Publication Data

US 2023/0184778 A1 Jun. 15, 2023

Related U.S. Application Data

(60) Division of application No. 17/349,710, filed on Jun. 16, 2021, now Pat. No. 11,609,233, which is a (Continued)

(51) Int. Cl.
*G01N 33/53* (2006.01)
*G01N 21/77* (2006.01)
(Continued)

(52) U.S. Cl.
CPC ......... *G01N 33/5302* (2013.01); *G01N 21/77* (2013.01); *G01N 33/5094* (2013.01);
(Continued)

(58) Field of Classification Search
CPC .............. G01N 33/582; G01N 33/5302; G01N 33/536; G01N 33/585
See application file for complete search history.

(56) References Cited

U.S. PATENT DOCUMENTS

| 9,041,790 B2 | 5/2015 | Fine et al. |
| 9,075,225 B2 | 7/2015 | Fine et al. |

(Continued)

FOREIGN PATENT DOCUMENTS

| CN | 1635988 | 7/2005 |
| CN | 105143886 | 12/2015 |

(Continued)

OTHER PUBLICATIONS

Moon et al. Lensless imaging for Point of Care Testing. Conf Proc IEEE Eng Med Biol Soc. 2009: 6376-6379. doi:10.1109/EMBS.2009.5333765 (Sep. 2009).*

(Continued)

*Primary Examiner* — Gailene Gabel
(74) *Attorney, Agent, or Firm* — Fish & Richardson P.C.

(57) ABSTRACT

An indicator of a first type and an indicator of a second type are attached to a unit of a chemical component in a sample to form a first multi-indicator complex. The first multi-indicator complex includes the unit of the chemical component, the indicator of the first type, and the indicator of the second type. The indicator of the first type and the indicator of the second type have different discernible characteristics. An image of the sample, including the first multi-indicator complex corresponding to the unit of the chemical component, is captured by an image sensor. Based on a first image of the sample, a count is generated of multi-indicator complexes that include an indicator of the first type and an indicator of the second type, including the first multi-indicator complex. Based on the count, a presence or a level of the chemical component in the sample is identified.

7 Claims, 8 Drawing Sheets

Related U.S. Application Data continuation-in-part of application No. 16/868,270, filed on May 6, 2020, now Pat. No. 11,099,181, and a continuation-in-part of application No. 16/845,458, filed on Apr. 10, 2020, now Pat. No. 11,255,850, said application No. 16/868,270 is a division of application No. 16/368,707, filed on Mar. 28, 2019, now Pat. No. 10,684,278, said application No. 16/845,458 is a continuation-in-part of application No. 16/368,707, filed on Mar. 28, 2019, now Pat. No. 10,684,278.

(51) Int. Cl.
  G01N 33/50   (2006.01)
  G01N 33/536  (2006.01)
  G01N 33/543  (2006.01)
  G01N 33/58   (2006.01)

(52) U.S. Cl.
  CPC ......... G01N 33/536 (2013.01); G01N 33/543 (2013.01); G01N 33/54313 (2013.01); G01N 33/582 (2013.01); G01N 33/585 (2013.01)

(56) References Cited

U.S. PATENT DOCUMENTS

| | | | |
|---|---|---|---|
| 9,518,920 | B2 | 12/2016 | Fine et al. |
| 9,720,217 | B2 | 8/2017 | Fine et al. |
| 9,910,254 | B2 | 3/2018 | Fine et al. |
| 9,952,417 | B2 | 4/2018 | Fine |
| 9,989,750 | B2 | 6/2018 | Fine et al. |
| 10,107,997 | B2 | 10/2018 | Fine |
| 10,114,203 | B2 | 10/2018 | Fine et al. |
| 10,153,317 | B1 * | 12/2018 | Fine .................. H01L 27/14603 |
| 10,249,669 | B1 * | 4/2019 | Fine .................. H01L 27/14636 |
| 10,461,112 | B1 * | 10/2019 | Fine ........................ G01N 33/49 |
| 10,684,278 | B1 | 6/2020 | Fine |
| 10,991,744 | B2 * | 4/2021 | Fine ........................ G02B 21/00 |
| 11,099,181 | B2 | 8/2021 | Fine |
| 11,255,850 | B2 | 2/2022 | Fine |
| 11,609,233 | B2 | 3/2023 | Fine |
| 11,719,700 | B2 | 8/2023 | Fine |
| 2006/0216696 | A1 | 9/2006 | Goguen |
| 2011/0065209 | A1 | 3/2011 | Heil et al. |
| 2013/0157288 | A1 | 6/2013 | Kilfeather et al. |
| 2014/0152801 | A1 | 6/2014 | Fine et al. |
| 2016/0041200 | A1 | 2/2016 | Fine et al. |
| 2016/0187235 | A1 | 6/2016 | Fine et al. |
| 2017/0074870 | A1 * | 3/2017 | Konry .............. G01N 33/54366 |
| 2017/0293133 | A1 | 10/2017 | Fine et al. |
| 2018/0284416 | A1 | 10/2018 | Fine et al. |
| 2019/0054466 | A1 * | 2/2019 | Gershtein .......... G01N 15/1463 |
| 2019/0056384 | A1 | 2/2019 | Gershtein |
| 2019/0056385 | A1 | 2/2019 | Gershtein |
| 2019/0162648 | A1 | 5/2019 | Fine |
| 2020/0309772 | A1 | 10/2020 | Fine et al. |
| 2020/0309777 | A1 | 10/2020 | Fine et al. |
| 2021/0311037 | A1 | 10/2021 | Fine |
| 2021/0311038 | A1 | 10/2021 | Fine |
| 2022/0082557 | A1 | 3/2022 | Fine |
| 2022/0274109 | A1 | 9/2022 | Gershtein |
| 2022/0412968 | A1 | 12/2022 | Fine |
| 2023/0164299 | A1 * | 5/2023 | Fine ................... G02B 21/0008 348/79 |
| 2023/0288407 | A1 | 9/2023 | Fine |

FOREIGN PATENT DOCUMENTS

| | | |
|---|---|---|
| CN | 113631912 | 11/2021 |
| TW | I641371 | 11/2018 |
| TW | I642780 | 12/2018 |
| WO | WO 2000068692 | 11/2000 |
| WO | WO 2011026030 | 3/2011 |
| WO | WO 2011102903 | 8/2011 |
| WO | WO 2012061778 | 5/2012 |
| WO | WO 2013057634 | 4/2013 |
| WO | WO 2020191480 | 10/2020 |
| WO | WO 2021203201 | 10/2021 |

OTHER PUBLICATIONS

Appleblom et al., "Homogeneous TR-FRET High-Throughput Screening Assay for Calcium-Dependent Multimerization of Sorcin", www.sbsonline.org, Society for Biomolecular Sciences, 2007, 7 pages.

Barua et al., "Challenges associated with Penetration of Nanoparticles Across Cell and Tissue Barriers: A Review of Current Status and Future Prospects", Nano Today, Apr. 2014, 9(2):223-243.

Bidinosti et al., "Novel one step immunoassays to Quantify a-Synuclein: Applications for Biomarker Development and High-throughput Screening", Journal of Biological Chemistry 287(40):33691-33705, Sep. 28, 2012, 16 pages.

Chang et al., "Novel Diagnostic and Predictive Biomarkers in Pancreatic Adenocarcinoma", International Journal of Molecular Sciences, Mar. 2017, 14 pages.

Chavda et al., "A Bead Aggregation Assay for Detection of Low-Affinity Protein-Protein Interactions Reveals Interactions between N-Terminal Domains of Inositol 1,4,5-Trisphosphate Receptors", PLOS/One, Mar. 2013, 7 pages.

Extended European Search Report in European Appln. No. 20779367.0, dated May 2, 2022, 11 pages.

Hashizume et al., "Openings Between Defective Endothelial Cells Explain Tumor Vessel Leakiness", Am. J. Pathol., Apr. 2000, 156(4):1363-1380.

International Preliminary Report on Patentability in International Application No. PCT/CA2021/050466, mailed on Oct. 20, 2022, 8 pages.

International Search Report and Written Opinion in International Application No. PCT/CA2020/050286, dated Jun. 5, 2020, 9 pages.

Kattke et al., "FRET-based Quantum Dot Immunoassay for Rapid and Sensitive Detection of Aspergillus amstelodami" Sensors 2011, 15 pages.

Medintz et al., "Self assembled nanoscale biosensors based on quantum dot FRET donors", Nature Materials, Oct. 2003, 10 pages.

Miller et al., "Significance of Circulating Tumor Cells Detected by the CellSearch System in Patients with Metastatic Breast Colorectal and Prostate Cancer", Journal of Oncology, Dec. 2009, 8 pages.

PCT International Preliminary Report on Patentability in International Appln. No. PCT/CA2020/050286, dated Oct. 7, 2021, 6 pages.

PCT International Search Report and Written Opinion in International Appln. No. PCT/CA2021/050466, dated Jul. 27, 2021, 10 pages.

Shao et al., "Diagnostic Technologies for Circulating Tumour Cells and Exosomes", Bioscience Reports, Feb. 2016, 36(1):E00292.

Shi et al., "Nanoparticles based fluorescence energy transfer (FRET) for biosensing applications", Journal of Materials Chemistry B, Royal Society of Chemistry, 2015, 17 pages.

Tagit et al., "Fluorescence Sensing of Circulating Diagnostic Biomarkers Using Molecular Probes and Nanoparticles", ACS Sensors, pubs.acs.org/acssensors, Oct. 25, 2017, 16 pages.

Taiwanese Office Action in TW Appln. No. 109110649, dated Mar. 5, 2021, 19 pages with English translation.

Verma et al., "Covalent Immobilization of Doxorubicin in Glycine Functionalized Hydroxyapatite Nanoparticles for pH-Responsive Release", New Journal of Chemistry, 2018, Abstract Only.

Wikipedia.org [online], "Immunoassay", published on May 17, 2021, retrieved on Jun. 14, 2021, retrieved from URL<https://en.wikipedia.org/wiki/Immunoassay>, 7 pages.

Zeng et al., "Constructions of Silver Triangular Nanoplates-Quantum Dots FRET Systems", Scientific Reports, www.nature.com/scientificreports, May 20, 2016, 8 pages.

Zorko et al., "Cell Penetrating Peptides: Mechanism and Kinetics of Cargo Delivery", Adv. Drug Deliv. Rev. Mar. 2005, 57:529-545.

Extended European Search Report in European Appln. No. 21784000.8, dated Aug. 28, 2023, 8 pages.

(56) References Cited

OTHER PUBLICATIONS

Office Action in Chinese Patent Application No. 202180034404.0, dated Dec. 28, 2023, 13 pages (with English Translation).

* cited by examiner

FIG. 8A
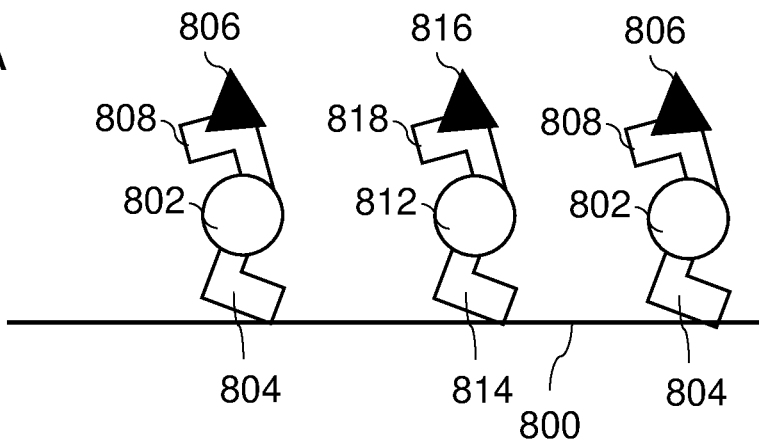
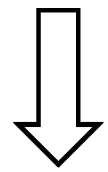
FIG. 8B
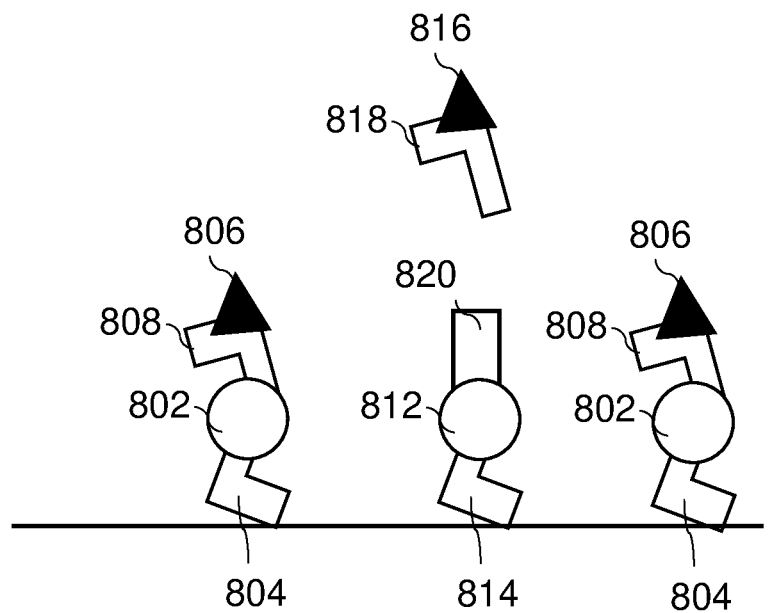

INDICATOR-BASED ANALYSIS OF A SAMPLE

CROSS-REFERENCE TO RELATED APPLICATIONS

This application is a divisional of and claims the benefit of priority to U.S. patent application Ser. No. 17/349,710, filed Jun. 16, 2021, which is a continuation-in-part of U.S. patent application Ser. No. 16/868,270, filed May 6, 2020, now issued as U.S. Pat. No. 11,099,181 on Aug. 24, 2021, which is a divisional of U.S. patent application Ser. No. 16/368,707, filed Mar. 28, 2019, now issued as U.S. Pat. No. 10,684,278 on Jun. 16, 2020. U.S. patent application Ser. No. 17/349,710, filed Jun. 16, 2021, is also a continuation-in-part of U.S. patent application Ser. No. 16/845,458, filed Apr. 10, 2020, now issued as U.S. Pat. No. 11,255,850 on Feb. 22, 2022, which is a continuation-in-part of U.S. patent application Ser. No. 16/368,707, filed Mar. 28, 2019, now issued as U.S. Pat. No. 10,684,278 on Jun. 16, 2020.

BACKGROUND

This description relates to indicator-based analysis of a sample.

To obtain all the useful information in a sample of whole blood of a patient for purposes of diagnosis, for example, requires not only a complete blood count (CBC) of the various types of blood cells in the blood sample and their hemoglobin content but also a chemical analysis of other components in the acellular portion of blood (e.g., the plasma). Such other components can include molecules and ions of various kinds.

Traditionally, both a CBC and a chemical analysis of blood are performed in a lab on large expensive machines using tubes of venous blood obtained by phlebotomy. Hours or days may be required for the chemical analysis to be completed and the results returned.

SUMMARY

This disclosure describes methods. In one aspect, this disclosure describes a method in which an indicator of a first type and an indicator of a second type are attached to a unit of a chemical component in a sample to form a first multi-indicator complex. The first multi-indicator complex includes the unit of the chemical component, the indicator of the first type, and the indicator of the second type. The indicator of the first type and the indicator of the second type have different discernible characteristics. One or more images of the sample, including the first multi-indicator complex corresponding to the unit of the chemical component, are captured by an image sensor. Based on at least a first image of the one or more images of the sample, a count is generated of multi-indicator complexes that include an indicator of the first type and an indicator of the second type, including the first multi-indicator complex. Based on the count, a presence or a level of the chemical component in the sample is identified.

Implementations of this and other methods may include any one or more of at least the following features.

In some implementations, the method includes situating the sample on a surface of the image sensor.

In some implementations, the indicator of the first type includes a bead.

In some implementations, the indicator of the first type includes a fluorescent label.

In some implementations, attaching the indicator of the first type and the indicator of the second type to the unit of the chemical component includes binding a first attachment unit and a second attachment unit to the unit of the chemical component. The first attachment unit is bound to the indicator of the first type, and the second attachment unit is bound to the indicator of the second type.

In some implementations, the first attachment unit and the second attachment unit are configured to bind to different locations on the unit of the chemical component.

In some implementations, the first attachment unit includes an antibody.

In some implementations, identifying the presence or the level of the chemical component in the sample includes determining a first number of indicators of the first type that are included in multi-indicator complexes that include an indicator of the first type and an indicator of the second type; determining a total number of indicators of the first type; and identifying the presence or the level based on the first number and the total number.

In some implementations, the method includes applying the first number and the total number to an empirically generated standard relationship to identify the presence or the level.

In some implementations, identifying the presence or the level of the chemical component in the sample includes determining a first number of indicators of the first type that are included in multi-indicator complexes that include an indicator of the first type and an indicator of the second type; determining a second number of indicators of the first type that are excluded from multi-indicator complexes that include an indicator of the first type and an indicator of the second type; and identifying the presence or the level based on the first number and the second number.

In some implementations, at least a portion of the second number of indicators of the first type are included in multi-indicator complexes that include an indicator type besides the first type and the second type.

In some implementations, at least a portion of the second number of indicators of the first type are singleton indicators.

In some implementations, capturing the one or more images of the sample includes situating the sample within a near-field distance of the image sensor.

In some implementations, the first type of indicator and the second type of indicator have different colors, absorption spectra, reflection spectra, observable surface properties, translucencies, emission spectra, excitation spectra, or a combination thereof.

In some implementations, the first type of indicator and the second type of indicator have different sizes, shapes, or both.

In some implementations, capturing the one or more images of the sample includes forming a monolayer of the sample.

In some implementations, each indicator of the first type includes two portions, and the two portions have different colors, absorption spectra, reflection spectra, observable surface properties, translucencies, emission spectra, excitation spectra, or a combination thereof.

This disclosure also describes apparatuses. In one aspect, this disclosure describes an apparatus that includes an image sensor, one or more processors, and one or more non-transitory, computer-readable media storing instructions that, when executed by the one or more processors, cause the one or more processors to perform operations. The operations include capturing, by the image sensor, one or more images of a sample. The sample includes a plurality of first multi-indicator complexes, each first multi-indicator complex including a unit of a chemical component, an indicator of a first type attached to the unit of the chemical component, and an indicator of a second type attached to the unit of the chemical component. The first type of indicator and the second type of indicator have different discernible characteristics. The operations include, based on at least a first image of the one or more images of the sample, generating a count of first multi-indicator complexes in the first image. The operations include, based on the count, identifying a presence or a level of the chemical component in the sample.

Implementations of this and other apparatuses may include any one or more of at least the following features.

In some implementations, the indicator of the first type includes a fluorescent label.

In some implementations, the indicator of the first type is attached to the unit of the chemical component by a first attachment unit, and the indicator of the second type is attached to the unit of the chemical component by a second attachment unit.

In some implementations, identifying the presence or the level of the chemical component in the sample includes determining a first number of indicators of the first type that are included in the plurality of first multi-indicator complexes; determining a total number of indicators of the first type; and identifying the presence or the level based on the first number and the total number.

In some implementations, the image sensor includes a surface configured to receive the sample, and an array of light-sensitive elements within a near-field distance of the surface.

In some implementations, identifying the presence or the level of the chemical component includes determining a first number of indicators of the first type that are included in the plurality of first multi-indicator complexes; determining a second number of indicators of the first type that are excluded from the plurality of first multi-indicator complexes; and identifying the presence or the level based on the first number and the second number.

In another aspect, this disclosure describes another method. The method includes attaching an indicator of a first type and an indicator of a second type to a unit of a chemical component in a sample to form a first multi-indicator complex. The first multi-indicator complex includes the unit of the chemical component, the indicator of the first type, and the indicator of the second type. Indicators of the first type and indicators of the second type have different discernible characteristics. The method includes capturing, by an image sensor, one or more images of the sample, including the first multi-indicator complex corresponding to the unit of the chemical component. The method includes, based on at least a first image of the one or more images of the sample, generating a count, in the first image, of multi-indicator complexes that include an indicator of the first type and an indicator of the second type, including the first multi-indicator complex. The method includes identifying a first plurality of indicators of the first type that are not included in multi-indicator complexes that include an indicator of the first type and an indicator of the second type. The method includes identifying a second plurality of indicators of the second type that are not included in multi-indicator complexes that include an indicator of the first type and an indicator of the second type. The method includes, based on the count, based on the identification of the first plurality of indicators of the first type, and based on the identification of the second plurality of indicators of the second type, identifying a presence or a level of the chemical component in the sample.

This disclosure also describes prepared samples. In one aspect, the disclosure described a prepared sample for imaging to determine a presence or a level of a chemical component in the prepared sample. The prepared sample includes a plurality of units of the chemical component. For each unit of the chemical component of the plurality of units of the chemical component, the prepared sample includes a first attachment unit bound at a first location on the unit of the chemical component and a second attachment unit bound at a second location on the unit of the chemical component, and an indicator of a first type bound to the first attachment unit and an indicator of a second type bound to the second attachment unit. Indicators of the first type and indicators of the second type have different discernible characteristics.

In another aspect, this disclosure describes another method. The method includes attaching a first indicator to a unit of a chemical component in a sample. The method includes attaching a second indicator, of a same indicator type as the first indicator, to one or more other indicators, to form a multi-indicator complex comprising the second indicator and the one or more other indicators. The method includes capturing, by an image sensor, one or more images of the sample. The method includes identifying, in at least a first image of the one or more images, the first indicator and the multi-indicator complex. The method includes, based on the identification of the first indicator and the multi-indicator complex, identifying a presence or a level of the chemical component in the sample.

Implementations of this and other methods may include any one or more of at least the following features.

In some implementations, the first indicator is attached to the unit of the chemical component by a first attachment unit that is bound to the first indicator and the unit of the chemical component; and the second indicator, within the multi-indicator complex, is bound to a second attachment unit of a same attachment unit type as the first attachment unit.

In some implementations, the method includes determining a first count of indicators of the same indicator type as the first indicator that are included in multi-indicator complexes in the first image, including the second indicator. The method includes determining a second count of indicators of the same indicator type as the first indicator that are not included in multi-indicator complexes in the first image, including the first indicator. The method includes, based on the first count and the second count, determining the level of the chemical component in the sample.

In some implementations, a lower first count corresponds to a higher level of the chemical component in the sample.

In some implementations, a higher second count corresponds to a higher level of the chemical component in the sample.

In another aspect, this disclosure describes another method. The method includes attaching a first indicator of a first type to a unit of a chemical component in a sample. The method includes capturing, by an image sensor, one or more images of the sample. The method includes identifying, based on at least a first image of the one or more images, a lack of an indicator of the first type at a first location on a surface of the image sensor or on a second surface. The method includes, based on identifying the lack of the indicator of the first type at the first location, determining a presence or level of the chemical component in the sample.

Implementations of this and other methods may include any one or more of at least the following features.

In some implementations, the method includes attaching a second indicator of the first type at a second location on the surface of the image sensor or on the second surface. The method includes identifying, based on the first image, the second indicator at the second location. The method includes determining the presence or the level of the chemical component in the sample based on identifying the second indicator at the second location.

In some implementations, the first location and the second location are included in a plurality of locations on the surface of the image sensor or on the second surface. The method includes determining, based on the first image, a first count of locations of the plurality of locations at which an indicator of the first type is located, including the second indicator. The method includes determining, based on the first image, a second count of locations of the plurality of locations at which an indicator of the first type is not located, including the first indicator. The method includes, based on the first count and the second count, determining the presence or the level of the chemical component in the sample.

In some implementations, a lower first count corresponds to a higher level of the chemical component in the sample.

In some implementations, a higher second count corresponds to a higher level of the chemical component in the sample.

In another aspect, this disclosure describes another method. The method includes attaching a unit of a chemical component in a sample to a location on a surface. The unit of the chemical component is attached to an indicator. The method includes capturing, by an image sensor, one or more images of the sample, including the unit of the chemical component attached at the location. The method includes identifying the indicator in at least one image of the one or more images of the sample. The method includes identifying, in the at least one image of the one or more images of the sample, the location at which the unit of the chemical component is attached on the surface based on the identification of the indicator. The method includes determining, based on a correspondence between the indicator attached at the location on the surface and the chemical component, a presence or a level of the chemical component in the sample.

These and other aspects, features, implementations, and advantages (1) can be expressed as methods, apparatus, systems, components, program products, business methods, means or steps for performing functions, and in other ways, and (2) will become apparent from the following description and from the claims.

BRIEF DESCRIPTION OF DRAWINGS

FIG. 8A is a schematic view of an example of surface-bound indicators.

FIG. 8B is a schematic view of an example of a competitive assay of a sample.

DETAILED DESCRIPTION

Figure 1:
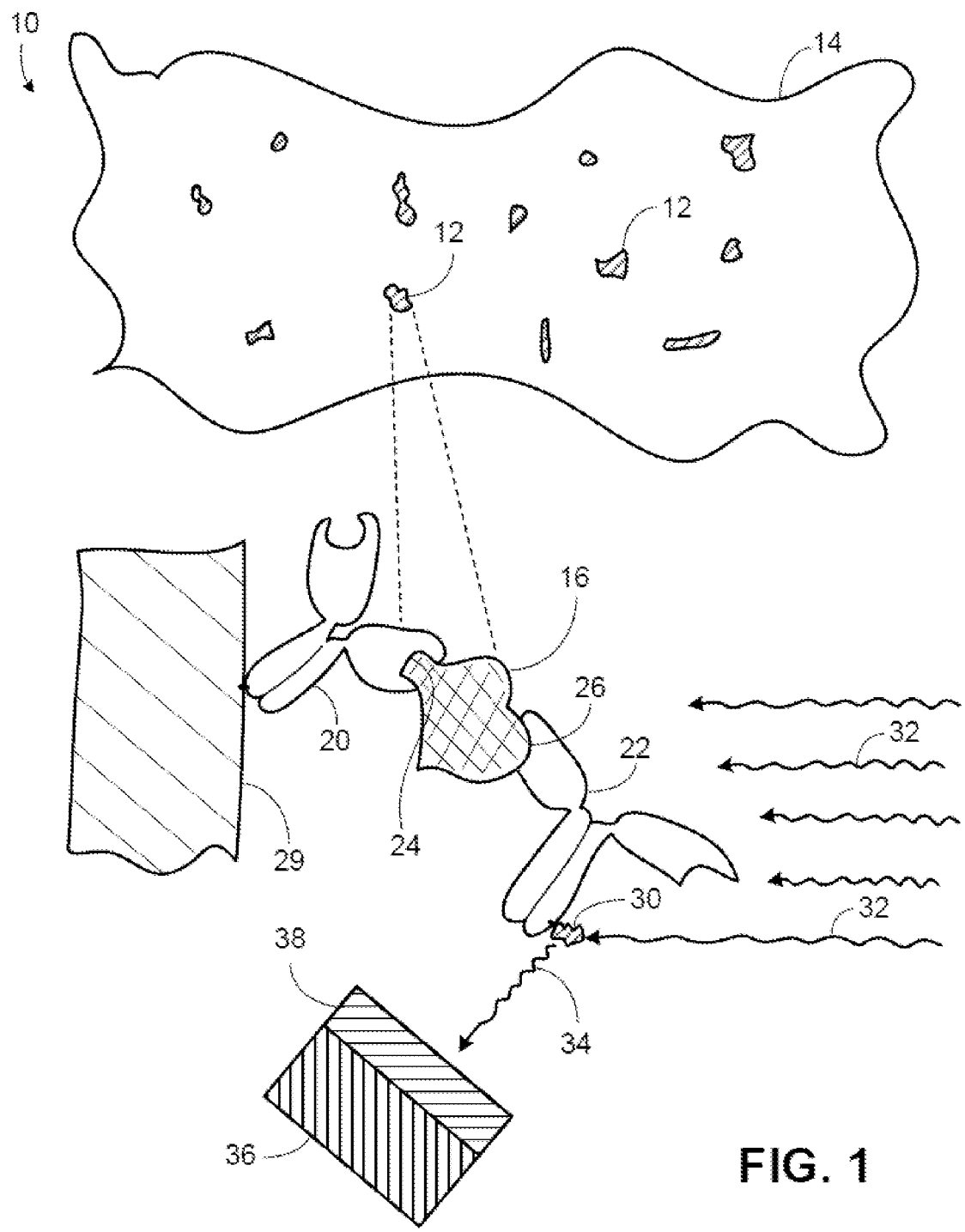
FIG. 1 is a schematic view of an example of a sample.

Here we describe a sample analysis technology that in some implementations can perform a chemical analysis of a sample of whole blood alone or in combination with a CBC directly at a point of care within a few minutes at low cost using a small portable easy-to-use, relatively inexpensive sample analysis device. In some uses, because of its small size and low cost, the sample analysis device can be reproduced in large numbers and distributed to many locations within one or more healthcare, residential, industrial, or commercial locations. In some applications, many units of the sample analysis device can be distributed and used in the field including at locations where equipment for sample analysis (for example, blood chemistry or CBC) is otherwise unavailable or prohibitively expensive.

We use the term "point-of-care" broadly to include, for example, any location in close physical proximity to a patient or other person to whom healthcare is being provided. In many cases, point-of-care refers to services provided in the physical presence of a patient, for example, in the same room or building or at the same place or within a short distance.

Although much of the discussion below refers to applications of the sample analysis technology to chemical analysis of whole blood drawn from a human or other animal, the sample analysis technology can also be applied to a wide range of contexts in which a sample (which may, but need not, be a biological sample) contains chemical components of interest (such as molecules or ions) and that may not involve counting and may or may not include particles, units, or other elements of one or more kinds that are to be counted.

We use the term "sample" broadly to include, for example, any fluid or other mass or body of material that contains one or more analyzable chemical components and may or may not also contain one or more countable units of one or more types. The countable units may in some cases be opaque, translucent, or otherwise non-transparent to incident light. The analyzable chemical components may in some instances be transparent, translucent, or otherwise non-opaque to incident light. In some examples, the sample is whole blood containing countable blood cells of different types and also containing analyzable chemical components such as molecules or ions, to name two.

We use the term "chemical components" broadly to include, for example, chemical compounds, ions, molecules, and other constituents of a sample that may not be present in a form of discernible (e.g., visible) countable units.

We use the term "unit of a chemical component" broadly to include, for example, a single unit of a chemical component such as a single molecule, ion, or other constituent. In typical samples, there are many units of a given type of chemical component, for example, many molecules of a chemical compound. Each occurrence (e.g., distinct unit) of a given particle, unit, complex or other element or group of elements may be referred to as an "instance" of the particle, unit, complex, or other element or group of elements.

We use the term "countable units" broadly to include, for example, elements present in a sample that are discrete, discernible, visible, identifiable, and subject to enumeration. Typically, countable units are not entirely transparent. In the case of whole blood, the countable units can include blood cells of different types.

We use the term "chemical analysis" broadly to include, for example, identification and quantification (e.g., determination of the level) of chemical components of one or more types in the sample. In some cases, chemical analysis can include identifying the presence of one or more molecules of one or more types and characterizing the amount, volume, or percentage of each of the types of molecules in the sample or in a particular volume of the sample.

As noted earlier, although the sample analysis technology has a broader range of applications, for convenience we sometimes discuss particular examples in which the sample comprises whole blood or components of whole blood.

We use the term "whole blood" broadly to include, for example, blood in its original form drawn from a human or other animal. Whole blood includes countable units such as blood cells and blood plasma that includes chemical components. As described in the Wikipedia entry titled "Blood plasma," blood plasma is "a yellowish liquid component of blood that normally holds the blood cells in whole blood in suspension. In other words, it is the liquid part of the blood that carries cells and proteins . . . . It is mostly water (up to 95% by volume), and contains dissolved proteins (6-8%) (e.g., serum albumins, globulins, and fibrinogen), glucose, clotting factors, electrolytes ($Na^+$, $Ca^{2+}$, $Mg^{2+}$, $HCO_3^-$, $Cl^-$, etc.), hormones, carbon dioxide (plasma being the main medium for excretory product transportation) and oxygen." Clotting factors include molecules such as plasminogen and prothrombin that participate in clot formation.

We use the term "blood cells" broadly to include, for example, red blood cells (erythrocytes), white blood cells (leukocytes), rare blood cell types, ambiguous blood cell types, and platelets (thrombocytes).

As shown in FIG. 1, typical automated techniques 10 for chemical analysis of blood use fluorescence-based sandwich immunoassay techniques to identify and quantify acellular chemical components 12, for example, molecules of one or more chemical components in blood plasma 14. The "filling" of the "sandwich" in fluorescence-based sandwich immunoassay is, for example, molecules 16 of a given target chemical component in the blood plasma. Each of the molecules is, in effect, sandwiched 18 as a result of adding two types 20, 22 of antibodies to the blood sample. The antibodies of one type 20 are known to bind specifically to one location 24 on the target molecules and serve as "capture antibodies" in the sense that they provide a known "base" at which the target molecules are held. The antibodies of the other type 22 serve as "detection antibodies" and are also known to bind specifically to the target molecules, but to a different location 26 on the target molecules. In some cases, the capture antibodies are fixed, e.g., to a surface 29, and literally "capture" the target molecules and hold them at a particular location on the surface. The detection antibodies are typically marked by fluorescent molecules 30 attached to them.

Once the target molecules have been captured, that is, bound to the capture antibodies, high intensity excitation light 32 illuminates the sample in one wavelength band causing much lower intensity light to be emitted 34 from the attached fluorescent molecules 30 in a different, typically longer, fluorescence wavelength band. The emitted light is sensed by a light detector 36 (usually after being passed through a filter 38 to block the much higher intensity excitation light). The light detector is highly sensitive to the presence and intensity level of the relatively low intensity fluorescence wavelength band light and can therefore generate signals indicating the fluorescence intensity and in turn the amount of the target chemical component present in the sample.

The fluorescence sandwich technique can be used to identify and quantify different target chemical components of blood simultaneously by using different appropriate pairs of capture antibodies and suitably labelled (by fluorescent molecules) detection antibodies. In some implementations of such multiplexing, the different capture antibodies are attached at different locations to a fixed surface as a way to differentiate the different target molecules based on their locations at the fixed surface. In some implementations, the target molecules remain dissolved or suspended in the sample and the different capture antibodies are marked using indicators such as fluorescent markers or fluorescent beads (for example, Luminex® beads) that produce fluorescence light in different wavelength bands, or different combinations of the bands, as a way to differentiate the different types of target molecules without regard to their locations in the sample.

As discussed throughout this disclosure, in some implementations of the sample analysis technology, chemical analysis is combined with a contact monolayer fluorescence and/or non-fluorescence imaging technique for performing a complete blood count (CBC). For several reasons, the standard fluorescence sandwich technique just described may not be optimally compatible with the contact monolayer non-fluorescence CBC technique. One reason is that, in the contact CBC technique, the blood sample is typically in direct contact with or within a near-field or quasi-near-field distance of a light-sensitive surface of an image sensor, which may preclude the inclusion of a filter element between the surface and the sample to block the high intensity excitation light. A second reason is that the contact CBC technique is not readily compatible with washing and other processing steps (one of which involves removing non-transparent blood cells from the sample) generally required in fluorescence sandwich immunoassay techniques. The washing and processing steps cannot be easily applied if the same whole blood sample used for the sample analysis technique is to be used also for the contact CBC technique. In comparison, as will be discussed later, because some implementations of contact CBC make use of a monolayer or other thin layer of blood, portions of the monolayer are free of blood cells and contain only light-passing blood plasma. Therefore, although the entire area of the image sensor may not be suitable for chemical analysis of the target molecules because of the presence of blood cells, some portions of the area of the image sensor are suitable for the sample analysis technique even with whole blood. A third reason why the fluorescent sandwich technique may not be optimally compatible with the contact CBC technique described above is that the small size pixels of the high-resolution image sensor do not provide as adequate low-light sensitivity to detect the low intensity emitted fluorescence light as can a larger-area light detector.

The sample analysis technology that is described here can be used independently to perform chemical analysis of whole blood or can be used to perform chemical analysis of whole blood in combination with or to supplement (simultaneously or sequentially) a contact CBC technique that uses the same sample and light from the same light source. As a result, both the contact CBC technique and the blood chemical analysis can be performed quickly at essentially the same time on a tiny sample of whole blood (for example, a sample of less than 50 microliters or less then 15 microliters or less then 5 microliters) at the point-of-care using a small inexpensive device. Although we often discuss examples in which the chemical analysis is performed on whole blood, the sample analysis technology can be applied to raw whole blood or to whole blood that has been processed to alter or adjust or remove or supplement chemical components or to whole blood from which some or all of the blood cells have been removed, including blood plasma.

We use the term "contact CBC technique" broadly to include, for example, any technique in which blood cells of one or more types are identified and counted in a sample that is in contact with (e.g., within a near-field distance of) a surface of an image sensor. Additional information about contact CBC techniques can be found in one or more of United States patent publications 2016/0041200, 2014/0152801, 2018/0284416, 2017/0293133, 2016/0187235, U.S. Pat. Nos. 9,041,790, 9,720,217, 10,114,203, 9,075,225, 9,518,920, 9,989,750, 9,910,254, 9,952,417, and 10,107,997, and U.S. patent application Ser. No. 17/193,680, all of which are incorporated here by reference.

However, note that the methods and systems described herein need not be used in conjunction with contact microscopy, near-field imaging, or thin layers (e.g., monolayers) of sample. Rather, in some implementations the disclosed methods and systems may be used in conjunction with other microscopy methods such as, e.g., using macroscopic lenses or flow cytometry to image thick (many-layer) samples.

Figure 2:
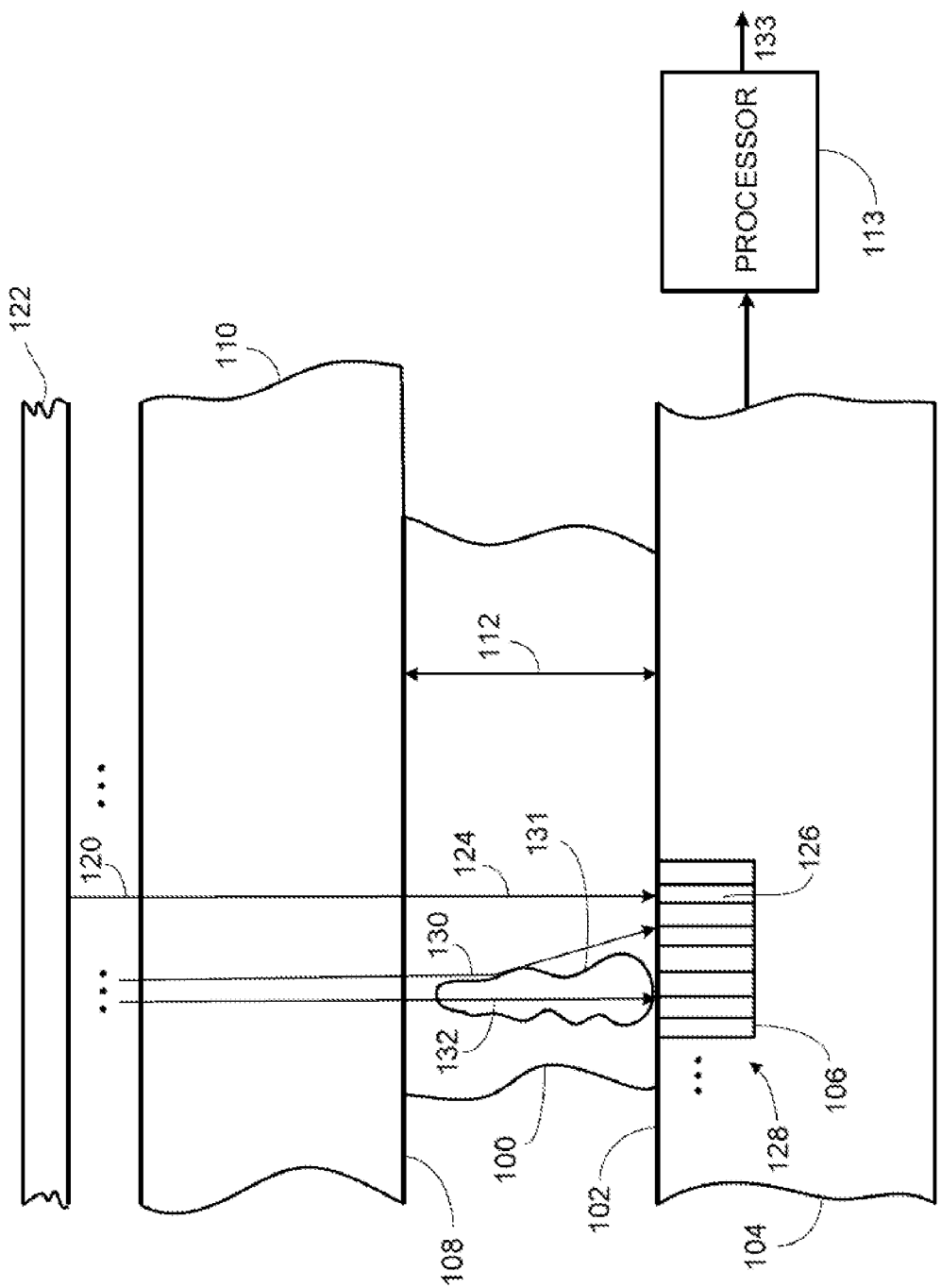
FIG. 2 is a schematic view of an example of chemical analysis of a sample.

Referring to FIG. 2, in some implementations of the sample analysis technology, a thin layer 100 (e.g., a monolayer) of whole blood is situated between a surface 102 of a high resolution image sensor 104 at which an array of photosensitive elements (e.g., pixels) 106 are exposed or within a near-field or quasi-near-field distance and a corresponding surface 108 of a lid 110, to form a thin layer having a known volume defined by its length, width, and thickness 112 between the surface 102 and the surface 108. Examples of structures and techniques for forming such a thin layer are described in one or more of United States patent publications 2016/0041200, 2014/0152801, 2018/0284416, 2017/0293133, 2016/0187235, and in U.S. Pat. Nos. 9,041,790, 9,720,217, 10,114,203, 9,075,225, 9,518,920, 9,989,750, 9,910,254, 9,952,417, and 10,107,997, and in U.S. patent application Ser. No. 17/193,680, all of which are incorporated here by reference.

In some implementations, before one or more images are captured of a sample, and/or between capturing images of the sample, the surface 108 can be repeatedly raised and lowered with respect to the surface 102, to cause the sample to be mixed. With or without prior mixing, the surface 108 is brought to a predetermined height with respect to the surface 102 to form the thin layer of the sample. When the thin layer of the sample is formed, unbound indicators (e.g., unbound beads) may be preferentially directed out from between the surface 102 and the surface 108. This may obviate the need for cumbersome rinsing steps that may be otherwise necessary. The formation of a thin layer may also make identification of multi-indicator complexes, singleton indicators, and indicators attached at specific surface locations more accurate and/or rapid, because fewer indicators may be present per unit imaged lateral area of the sample.

We use the term "high-resolution" broadly to include, for example, an image sensor that has a pixel spacing in one or both of two dimensions that is smaller than 5 μm, or 3 μm, or 1 μm, or sub-micron, for example.

We use the term "thin layer" broadly to include, for example, a volume of a sample that has a thickness no greater than the thickness of a particular type of unit in the sample, such as blood cells, so that across the thin layer two units cannot be stacked in the dimension defined by the thickness. In the case of a whole blood sample, the thickness of the thin layer could be in the range of 1 micrometer to 100 micrometers.

Light 120 from a light source 122 illuminates the monolayer 100. Portions 124 of the light may pass through the sample monolayer and be received by photosensitive elements 126 in the array 128 of the image sensor. Portions 130 of the light may be reflected or refracted by components 131 of the monolayer and the reflected or refracted light may be received by photosensitive elements in the array. Portions 132 of the light may be transmitted through components of the monolayer and the transmitted light may be received by photosensitive elements in the array; portions of the light may be absorbed by components of the monolayer. As discussed later, the components of the monolayer can include countable units, chemical components, beads, indicators, attachment units, and other elements.

The light source can be configured or controlled or both to provide illuminating light in one or more selected wavelength bands and combinations of them. A wide variety of types of light sources and combinations of them can be used, for example, LEDs, LED panels, organic LEDs, fluorescent panels, incandescent lamps, ambient illumination, arrays of monochrome LEDs, arrays of narrowband sources such as red, green, and blue LEDs or lasers, a miniaturized color display such as a liquid crystal or organic LED (OLED) display or an RGB laser color projector.

Using the light that originates at the light source and passes through, is reflected or refracted by, or is transmitted through the monolayer, the image sensor captures one or more images of the monolayer including countable units of various types (for example, blood cells) and chemical components that are detectable (either in their native condition or as a result of being marked as discussed later). One or more of the captured images are processed by one or more processors or other image processing components 113 to produce information 133 about the whole blood sample including, for example, a CBC or a chemical analysis or both of the countable units and chemical components. Among other things, the resulting information can include a count of red blood cells and their hemoglobin content.

The CBC information can be generated by identifying and counting in the captured images the number of countable units of each type in the sample. Additional information about CBC techniques and about imaging using contact image sensors can be found, for example, in United States patent publications 2016/0041200, 2014/0152801, 2018/0284416, 2017/0293133, 2016/0187235, and in U.S. Pat. Nos. 9,041,790, 9,720,217, 10,114,203, 9,075,225, 9,518,920, 9,989,750, 9,910,254, 9,952,417, 10,107,997, all of which are incorporated here by reference.

Figure 3:
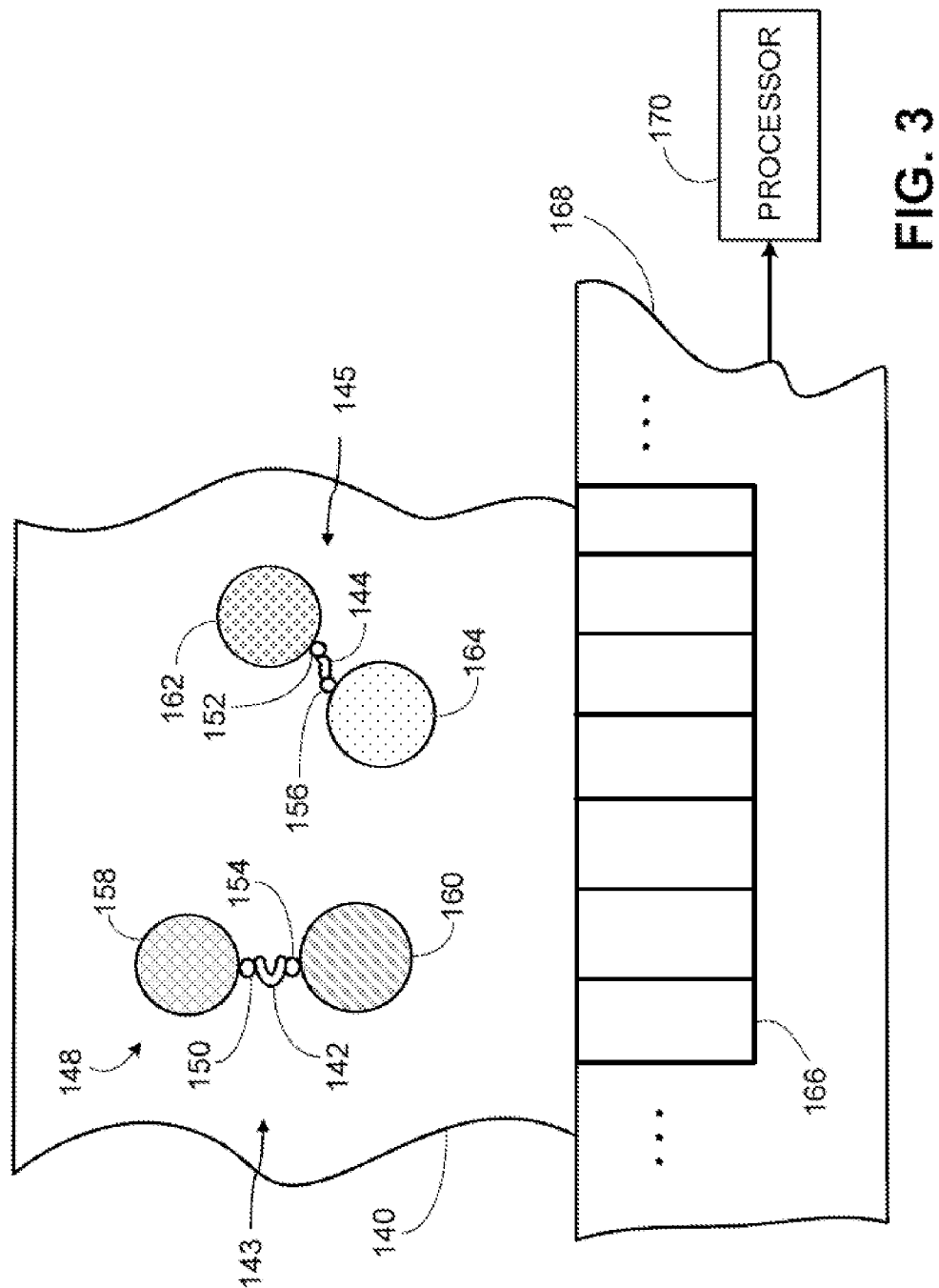
FIG. 3 is a schematic view of an example of chemical analysis of a sample.

As shown in FIG. 3, a monolayer 140 of whole blood (such as the same monolayer of whole blood used for the contact CBC technique) can be used for chemical analysis of various chemical components 142, 144 of the whole blood. For this purpose, individual units of the different types of chemical components of the whole blood monolayer sample can be treated as fillings of sandwiches 148 similar to the fluorescent sandwiches. However, in some implementations of the sample analysis technology described here, capture antibodies 150, 152 and detection antibodies 154, 156 are attached to beads 158, 160, 162, 164 that need not have fluorescent properties and are directly visible or otherwise detectable using light that originates at the light source and passes through, is reflected or refracted by, or is transmitted through the monolayer or components of the monolayer.

In the example of FIG. 3, the beads 158, 160, 162, 164 have different light absorption and/or reflection characteristics, such that complexes of bead-bound chemical components are defined and identified (e.g., identified by a computer system that receives an image of the complexes) not only by the presence of multiple beads in a close proximity but also by a particular combination of bead types attached to each chemical component and/or by the fact that the beads bound to each chemical component are different. Beads of different types may instead or additionally differ from one another in other ways, e.g., by size, shape, or another discernable characteristic.

In some implementations, beads within a multi-bead complex are of the same type and may be identified based on a proximity of the beads within the multi-bead complex to one another.

Some implementations described in this disclosure refer to beads, e.g., complexes of direct indicator beads. Beads are examples of "indicators." Indicators include at least elements that can be caused to attach to units of chemical components in a sample and which can be detected in images of the sample. Other types of indicators, besides direct-indicator beads, include fluorescent markers, e.g., fluorescent markers on attachment units such as antibodies.

Descriptions in this disclosure of multi-bead complexes can equally describe multi-indicator complexes that include, for example, two or more indicators. A multi-indicator complex may include, for example, one or more beads and one or more non-bead indicators (e.g., fluorescent labels), two or more fluorescent labels, etc.

Multi-indicator complexes (of which multi-bead complexes are a particular case) can be formed and identified as described for multi-bead complexes throughout this disclosure, e.g., based on identifying a proximity of two or more indicators and/or identifying a combination of two or more types of indicator.

Referring again to FIG. 3, the resulting light is received by light-sensitive elements (e.g., pixel) 166 arrayed in the image sensor 168. For some implementations of direct-indicator beads without fluorescence, unlike for fluorescence-based techniques, the light source is not within the monolayer sample but is external to it.

Using the received light, the image sensor captures one or more images of the monolayer sample. One or more processors 170 or other image processing devices process the one or more received images and apply a variety of techniques to identify the presence of and determine the level (e.g., quantity, amount, volume, percentage) of each of the chemical components in the sample, as described throughout this disclosure.

The beads 158, 160, 160, 162 to which the antibodies 150, 152 and 154, 156 are attached may have, but need not have, fluorescent properties. The beads can have characteristics that are detectable, visible, or otherwise discernible based on light from the light source that is reflected from, refracted by, or passes through them. We sometimes refer to such beads, which are directly visible in captured images through the light that is reflected from, refracted by, or passes through them, as opposed to light originating in them, as "direct indicator beads". The direct indicator beads can take the form of what are sometimes call microbeads in reference to their small size. Microbeads have sizes typically in the range of 0.5 to 500 micrometers.

We use the term "indicator" broadly to include, for example, any tag, marker, or other indicator device or indicator characteristic that can be attached to or associated with a chemical component of a sample and is identifiable at a sensor using received light that was incident on and reflected or refracted by or transmitted through the indicator device or characteristic. In some cases, direct indicator beads can take the form of small grains, particles, beads, spherules, or other elements, and combinations of them, and can be of a variety of shapes, sizes, materials, and colors. Other types of indicators can take the form of fluorescent labels (e.g., tags) included in or attached to attachment units.

To determine the presence of units of chemical components in the sample, the processor analyzes the images to detect directly discernible characteristics of beads and complexes of two or more beads that are revealed by light originating from the light source and reflected from, refracted by, or transmitted through the beads to the surface of the image sensor.

We use the term "directly discernible characteristics" of beads and complexes of beads broadly to include, for example, any quality, attribute, or other trait that can be detected, determined, or derived from light that originated at a light source and was reflected from, refracted by, or transmitted through the beads. Directly discernible characteristics could include color, size, texture, birefringence, or shape, or combinations of them, for example.

We use the term "complexes of beads/indicators" broadly to include, for example, two or more beads/indicators that can be associated with one another because they are attached to a unit in a sample, such as a molecule or other chemical component. Typically, the two or more beads/indicators of a complex are detectable in constant close proximity (e.g., touching or within a predetermined distance) to one another. In some cases, the two or more beads/indicators of a complex are detectable because they have two or more predetermined different directly discernible characteristics. For example, two beads of a complex may have two specific different colors that are discernible by processing the images from the image sensor.

Indicators may instead, or additionally, be detected based on light originating at the indicators themselves, e.g., fluorescence emitted by the indicators.

We use the word "attach" to include both direct and indirect attachment. For example, two particles, units, beads, indicators, or other elements may be attached directly (e.g., in contact and bound) to one another, or indirectly (e.g., attached to one another by an attachment unit bound to each of the two particles, units, or other elements).

We use the term "attachment unit" broadly to include, for example, any antibodies (e.g., an antibody directed against a cluster-of-differentiation cell surface antigen if the target unit is a specific cell type), capsid proteins or other antigens from a pathogenic virus (e.g., if the target unit is an antibody to the pathogenic virus, indicating prior exposure to the pathogenic virus), and other binding molecules and structures suitable for binding or attachment (e.g., direct attachment) to a unit of a chemical component. "Capture antibodies" and "detection antibodies," described in reference to several implementations according to this disclosure, are non-limiting examples of attachment units.

The sample analysis technology that we describe here can be applied in a variety of different modes.

In some examples of one such mode, which we sometimes call the complexed-indicator mode or complexed-bead mode, the chemical components remain dissolved or suspended in the sample. A first attachment unit and a second attachment unit, each coupled to a separate direct indicator bead or other indicator, bind simultaneously to two different locations on a given target molecule or other unit of a target chemical component to form a complex of two indicators (i.e., a doublet).

In the case of direct indicator beads, because each direct indicator bead may have more than one of its particular (capture or detection) antibody bound to its surface, a bead may participate in more than one such complex simultaneously.

By processing one or more images captured by the image sensor, it is possible to identify those beads or other indicators present in doublets or higher-order complexes, and thus associated with the chemical component. By determining the proportion of complexed beads or other indicators to the total number of beads or other indicators (complexed and singleton, that is, uncomplexed) identified in the sample, it is possible to determine the level or amount or quantity or concentration of the target units (e.g., molecules) of the chemical component in the sample.

It is true that identified singleton beads or other indicators are not necessarily beads or indicators unbound to the target molecule, because in some cases only the capture antibody or the detection antibody, but not both, may have bound to the target molecule.

However, under constant incubation conditions and provided that the concentrations of indicator-coupled first attachment units and indicator-coupled second attachment units in the sample are constant and their ratio is known, it is possible empirically to establish a "standard curve" that represents the relationship between a complex index (that is, a proportion of complexed beads or other indicators to total beads or other indicators identified by the device) and the concentration of the target molecule.

Figure 4:
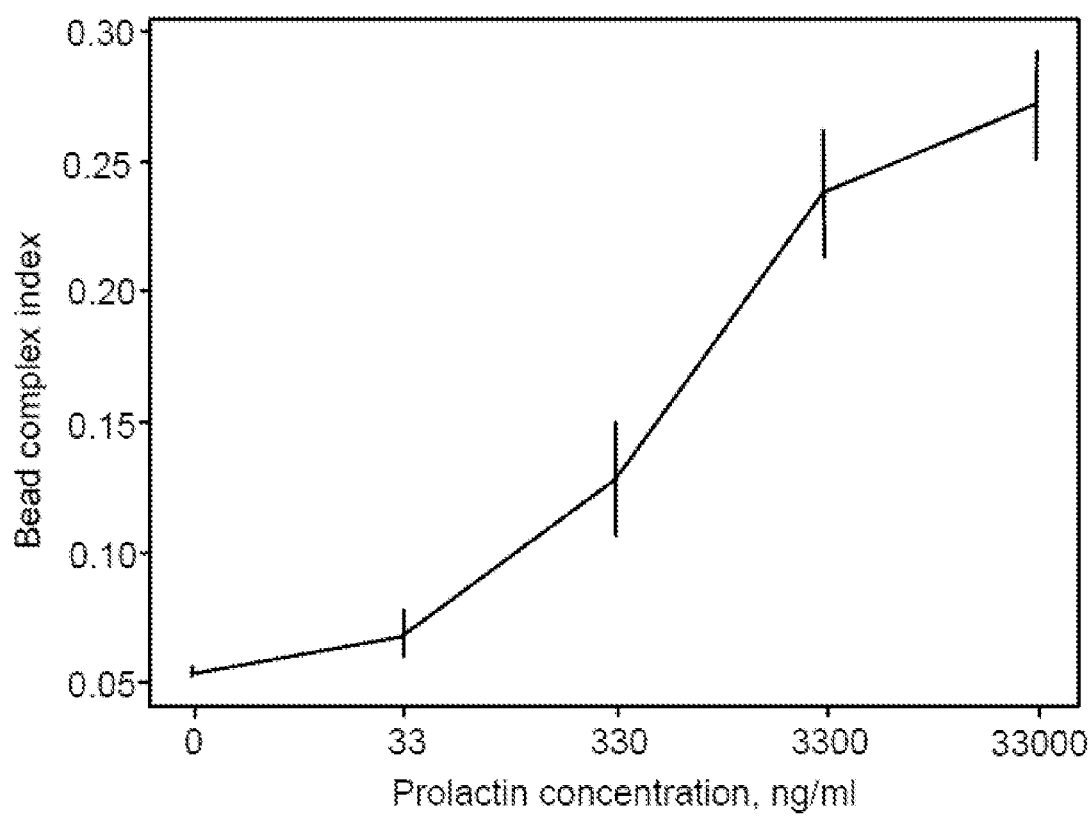
FIG. 4 is a graph of a standard curve.

This has been done experimentally for prolactin to generate the standard curve shown in FIG. 4. Using the standard curve, it is possible to determine the otherwise unknown concentration of prolactin in a sample by determining the complex index under identical incubation conditions.

In some implementations, the same indicators can be used to mark both the first attachment units and the second attachment units that will bind to given instances of the chemical component.

However, indicators may sometimes adhere to other indicators non-specifically, i.e., in the absence of sandwiched target units. Contribution of such non-specific binding to the complex index may be reduced by using different beads or other indicators for first and second attachment units, and excluding counts of complexes between beads or other indicators of the same type; rather, in this implementation, only complexes between two or more different beads or other indicators, and/or only complexes where particular combinations of different beads or other indicators are identified, are counted.

In some implementations, by using complexes of various beads or other indicators having different directly discernible characteristics for first attachment units and second attachment units that are to be attached to the units of different chemical components, it is possible to multiplex the process of detecting the presence and levels of the different chemical components at the same time. Multiplexing can be achieved by using beads having different colors, sizes, shapes, textures, or other directly discernible characteristics, and/or by using indicators having different discernible characteristics. For example, different types of fluorescent markers may emit light of different wavelengths and/or emit light in response to being illuminated by light of different wavelengths.

In some implementations, the target unit of the chemical component includes at least one of an antigen, a hormone, a biomarker, a drug, a viral capsid, a pathogen-directed antibody (for example, a virus-directed antibody), an oligonucleotide, or another molecule, cell, or particle.

In some implementations, a bead or other indicator is bound to, attached to, or otherwise associated with an attachment unit, and the attachment unit is bound to the target unit of the chemical component. Referring back to the example of FIG. 3, attachment units 150 and 154 are bound to a first target unit 142 of a first chemical component, and attachment units 152 and 156 are bound to a second target unit 144 of a second chemical component. Beads 158 and 160 are bound to attachment units 150 and 154, respectively, to form a multi-bead complex 143 that includes beads 158 and 160, attachment units 150 and 154, and target unit 142. Beads 162 and 164 are bound to attachment units 152 and 156, respectively, to form a multi-bead complex 145 that includes beads 162 and 164, attachment units 152 and 156, and target unit 144. In some implementations, it is the proximity of the beads 162 and 164 to one another or the constancy of the proximity or both that allows for the identification of the multi-bead complex. The proximity can be measured in terms of absolute distance, or proportion of the dimension of one or more of the beads, for example.

The attachment units 150, 152, 154, 156 can be, but need not be, detection antibodies or capture antibodies. In addition to, or alternatively to, antibodies, the attachment units 150, 152, 154, 156 may include a capsid protein or other antigen of a pathogenic virus. The attachment units 150, 154 may be different from one another.

The target units 142 and 144 of the chemical component may include at least one of an antigen, a hormone, a biomarker, a drug, a viral capsid, a pathogen-directed antibody (for example, a virus-directed antibody), an oligonucleotide, or another molecule, cell, or particle. The attachment units 150, 152 (for example) may include proteins of a virus, the proteins binding to an antibody 142 to the virus.

As noted above, in some implementations, the beads 158, 160 of a given complex are different from one another in one or more discernible characteristics such as size, color, absorption spectrum, reflection spectrum, shape, observable surface properties, translucency, and combinations of these characteristics. In captured images, the different discernible characteristics may be indicated by, for example, different hues, intensities, and/or saturation values of the beads in the images, or by other visual characteristics of the beads in the images. As noted throughout this disclosure, different discernible characteristics (e.g., different output light wavelengths or different fluorescence-exciting input light wavelengths) of other types of indicators may also be used.

Some bead types may be divided into two or more portions, each portion having different respective discernible characteristics. For example, a first hemisphere of a given bead may have a first absorption spectrum, and a second hemisphere of the bead may have a second, different absorption spectrum.

In some implementations, instead of, or in addition to, proximity-based multi-indicator complex identification, multi-indicator complexes are identified based on the detection of a particular combination of different indicator types.

As a non-limiting example of such identification, bead types A, B, C, D each have different discernible characteristics. The beads are bound, or are configured to bind, to attachment units configured to bind to different types of chemical components. Specifically, the beads and attachment units are configured such that bead types A and B will become attached to, and form a multi-bead complex including, a first chemical component, and bead types C and D will become attached to, and form a multi-bead complex including, a second chemical component. After sample imaging, bead complexes with other combinations (e.g., A and A, or A and C) are ignored or otherwise discounted when using standard curves and other methods to determine a presence and/or concentration of the first and second chemical components.

Note that, in some implementations, bead and attachment units may be configured such that a bead type attaches to more than one type of chemical component. Identification of one or more other, targeted bead types in a multi-bead complex with the bead type allows for identification of the chemical component in the multi-bead complex. For example, bead types A and B may indicate a first chemical component, and bead types A and C may indicate a second chemical component.

Ratios of different bead types of may also be used for identification. For example, a first chemical component may form complexes with two A-type beads and one B-type bead, while a second chemical component may form complexes with one A-type bead and two B-type beads, with three beads in each multi-bead complex for each unit of the first chemical component or second chemical component.

Moreover, as further noted throughout this disclosure, in some implementations complexes are formed by indicators of a single type, e.g., a complex including two or more A-type beads and no beads of other types.

The ratio (called the complex index) of counted complexed indicators to the total number of counted indicators (the total being the complexed or aggregated indicators and the singleton un-complexed indicators) is indicative of the level or amount or quantity or concentration of the units (instances) of the target chemical component in the sample. The count discriminates between, in various implementations, complexed or aggregated beads or other indicators and singleton beads; complexes of multiple bead types and complexes of single bead or other indicator types; and/or complexes of multiple bead or other indicator types that include different respective combinations of bead or other indicator types. Taking into account bead or other indicator type (and not just multi-indicator presence) in analysis may be more accurate than assuming that all complexed beads or other indicators are bound to units of the target chemical component and that all singleton beads or other indicators are not bound to units of the chemical component. The results of the analysis can therefore take into account a) non-specific multi-indicator complexes not bound to target chemical components (e.g., bound to one another) and b) target chemical components to which only singleton indicators are bound. The latter effect may be relatively insignificant because very few target units are typically bound only to a singleton indicator. The former effect can impede the ability of the sample analysis technology to detect a low level amount or quantity or concentration of the target chemical component.

Many or virtually all of the non-specific indicator complexes (indicator complexes that do not include a target chemical component) are formed during the process of coupling the attachment units to the indicators and before the attachment units are bound to the units of the target chemical component, because more than one indicator may bind to a single attachment unit. Therefore, complexes of two or more different types of indicators identified in the imaged sample can be assumed to represent target molecules. The density of the indicators in the sample is low enough that the probability of two or more indicators of different types landing in contact with each other absent a target molecule may be very small, e.g., essentially zero. Therefore, by identifying, during image analysis, complexes including two or more different indicator types rather than simply multi-indicator complexes of any type, false-positive target chemical component identifications can be reduced, improving (for example, by more than ten times) the sensitivity and consistency of the sample analysis technology.

In addition, the identification of different combinations of indicator types included in multi-indicator complexes can allow for highly multiplexed analysis, with multi-indicator complexes including three, four, or more indicators in various combinations being used to identify and analyze tens, hundreds, or thousands of different chemical components in a sample.

The complex index described throughout this disclosure may be generalized to multiple indicator types and multiple types of multi-indicator complexes. For example, rather than considering a ratio of complexed indicators of a first type to a total number of indicators of the first type, the performed analysis may determine a number of indicators of two types included in multi-bead complexes that include indicators of the two types, and compare that number to a total number of indicators of the two types and/or to a number of singleton indicators of the two types. As another example, an analysis may include determining a number of indicators of the first type that are include in multi-bead complexes that include indicators of the type types, and compare that number to a total number of indicators of the first type and/or to a number of singleton indicators of the first type. Standard curves for expected indicator permutations may be determined as described in reference to FIG. 4.

Figure 5:
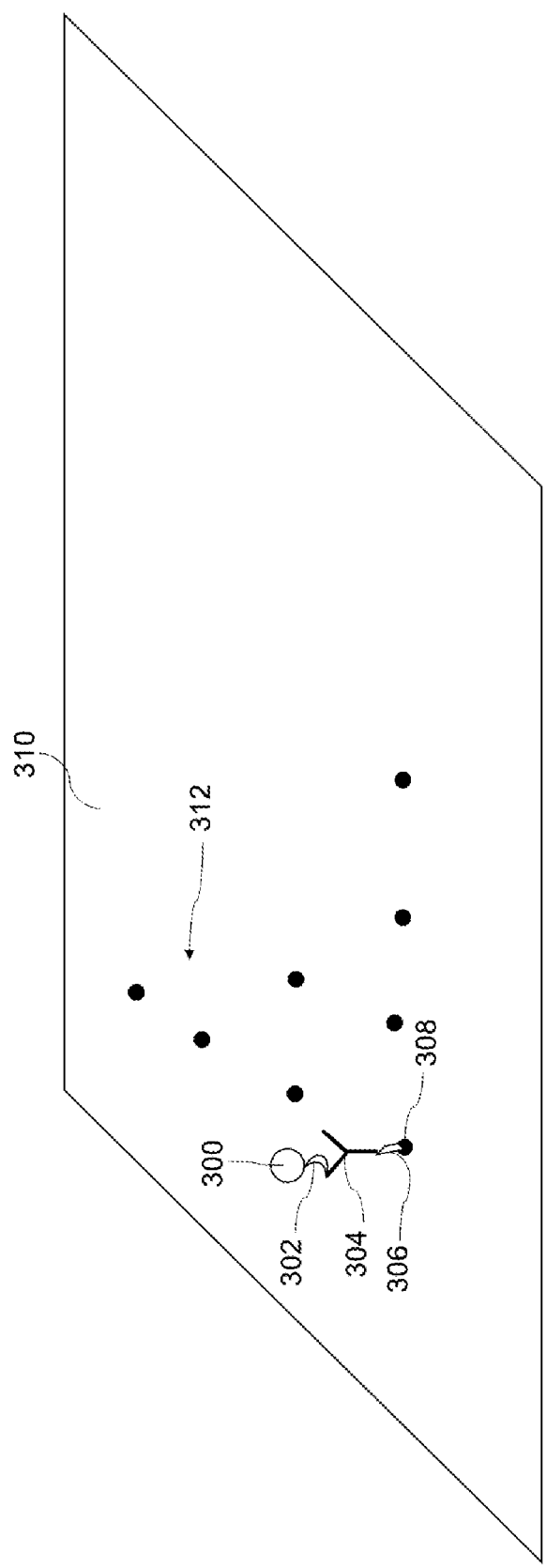
FIG. 5 is a schematic view of an example of chemical analysis of a sample.

As shown in FIG. 5, in some implementations, an attachment unit 306 (for example, a capture unit, capture particle, or other capture element) is bound at a known location 308 on a surface 310 (e.g., a surface of an image sensor, or a surface of a lid). The attachment unit 306 may be printed onto the surface 310. The surface 310 may include an array of known locations 312, each known location corresponding to a known type of attachment unit (not shown, except for 306). For example, correspondences between locations and types of attachment units may be stored in a storage device.

The attachment unit 306 is bound to a target unit 304 of a chemical component, which is bound to an attachment unit 302. The attachment unit 302 is bound to an indicator 300, e.g., a bead or a fluorescent label.

Images captured using incident light that passes through the sample and is reflected, refracted or transmitted by the indicators can then be processed to identify and determine the amounts of different types of chemical components based on the imaged locations of the indicators attached to the attachment units. This technique of chemical analysis can be used in combination with the contact CBC technique discussed earlier or with other imaging techniques.

Because the attachment unit 306 is of a known type (e.g., a type known to bind to the target unit 304 of the chemical component) and in a known location, imaging of the indicator 300 and determination of the known location 308 may be used to determine an amount or presence or both of the chemical component.

The attachment units 302 and 306 can be, but need not be, antibodies, and can include types of attachment units as described above in reference to FIG. 3, e.g., antigens. The target unit 304 of the chemical component may include at least one of an antigen, a hormone, a biomarker, a drug, a viral capsid, a pathogen-directed antibody (for example, a virus-directed antibody), an oligonucleotide, or another molecule, cell, or particle.

The surface 310 may be the surface 108 of the lid 110 that faces the surface 102 of the image sensor 104 and defines a gap occupied by the thin layer 100 of the sample, as described in reference to FIG. 2. When the thin layer of the sample is in the gap and in contact with the printed spots in the array of attachment units, respective chemical components in the sample will bind to respective attachment units, based on the type of the chemical components, in positions defined by the locations of the printed spots in the array.

In some implementations, a capture bead includes an attachment unit. In some implementations, a surface (for example, the surface 310) includes an attachment unit.

In some implementations, a combination of the location-based chemical analysis technique and the in-solution or in-suspension (that is, non-location-based, complexed-beads mode) chemical analysis technique could be used.

In order to use these chemical analysis techniques in combination with a CBC technique or other sample imaging technique in a point-of-care setting, steps may be taken to impart the bead-coupled attachment units to the sample before it is loaded onto the image sensor surface or as it is loaded onto the image sensor surface. One approach is to pass the sample through a tube where dried bead-coupled attachment units or attachment unites otherwise associated with indicators are solubilized by the sample and allowed to bind with target chemical components. Then the prepared sample can be placed on the sensor surface. Another approach is to deposit the indicator-coupled attachment units onto the surface 108 of the lid 110, onto the surface of the image sensor (in some cases in addition to indicator-free attachment units irreversibly bound at specific locations of the lid surface and/or surface of the image sensor), or onto another surface with which the sample will be put in contact, so that they are solubilized when the sample encounters that surface. The indicator-coupled attachment units may be dried or otherwise attached to the surface 108, the surface of the image sensor, and/or the other surface ahead of time.

Various choices of the target units and attachment units may be used in a variety of applications, such as cytometry, in vitro diagnostics, environmental analysis, multiplex biochemical assays, serology, and gene expression and combinations of them.

In an example of serology applied to a sample of blood from a patient, beads are bound to recombinant viral proteins of an infectious virus. The recombinant viral proteins bind to antibodies of the infectious virus within the sample. Complexes of two or more of the beads associated with an antibody of the infectious virus are identified or enumerated or both, and results of the identification or enumeration or both (potentially in concert with the identification or enumeration or both of single un-complexed beads) are used to determine a presence or level or both of the antibody of the infectious virus, as described earlier. Based on the determined presence or level or both of the antibody of the infectious virus, past exposure by the patient to the infectious virus can be identified. Samples besides blood may be used in addition to or instead of blood.

Some implementations according to this disclosure incorporate a competitive assay approach. In a competitive assay approach, instead of a target chemical component in a sample leading to the formation of multi-indicator complexes and/or indicators attached at specific locations on a surface, the presence of the target chemical component causes a decrease in multi-indicator complexes and/or a lack of indicators attached at the specific locations. The multi-indicator complexes and/or indicators attached at the specific locations are present in the sample in the absence of the target chemical component. When a target chemical component is present in the sample, the target chemical component displaces indicators from the multi-indicator complexes to form singleton indicators or lower-order multi-indicator complexes, and/or displaces indicators from the specific locations at which the indicators are known to be attached.

For example, in some competitive assay implementations, two or more indicators are each bound to a respective attachment unit, and the attachment units are attached to one another to form a multi-indicator complex having a first number of indicators. As described throughout this disclosure, the two or more indicators may be the same or different types of indicator. One or more of the attachment units is also configured to attach to the target chemical component, such that, when the target chemical component is present in the sample, at least one of the attachment units (and its corresponding indicator) may detach from the multi-indicator complex and instead attach to the target chemical component, leaving behind either a singleton indicator (e.g., if the multi-indicator complex was a doublet complex and one attachment unit detaches) or a multi-indicator complex with fewer indicators than the first number of indicators. When one or more images of the sample are captured and the indicators are identified, the relative decrease in indicators within multi-indicator complexes with the first number of indicators compared to singleton indicators or indicators in multi-indicator complexes with a fewer number of indicators than the first number can be identified, and a presence or level of the target chemical can be correspondingly determined. A standard curve or other relationship between these values can be predetermined experimentally using samples with known concentrations of the target chemical component, and the predetermined relationship can then be employed when imaging samples with unknown concentrations of the target chemical component.

Figure 6A:
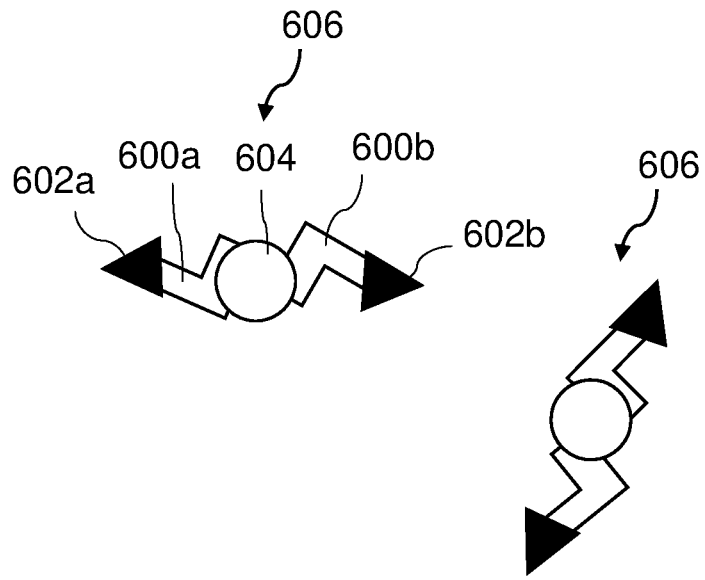
FIG. 6A is a schematic view of an example of complexed indicators.
Figure 6B:
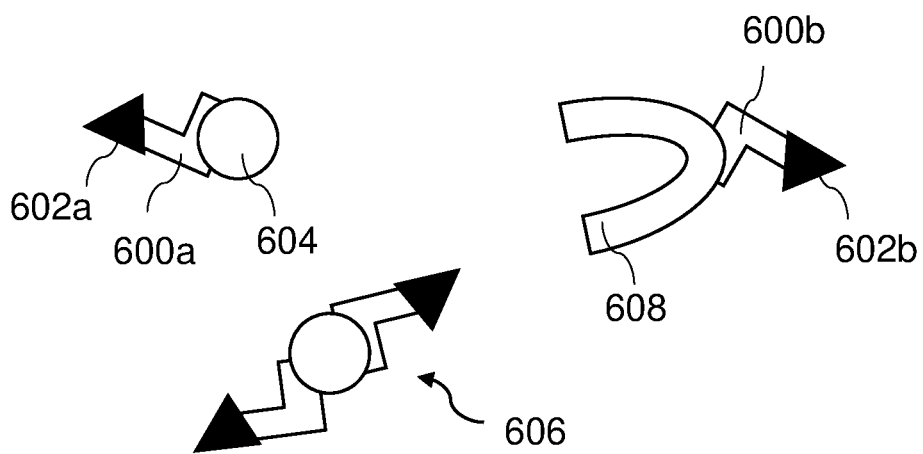
FIG. 6B is a schematic view of an example of a competitive assay of a sample.

In some immunoassay implementations, as shown in FIG. 6A, attachment units 600a, 600b (in this example, antibodies) are bound to respective indicators 602a, 602b (in this example, fluorescent indicators) and are each attached to a first binding element 604 (e.g., an antigen to the antibodies), to form a multi-indicator complex 606. As shown in FIG. 6B, a unit 608 of a target chemical component competitively binds to the attachment units 600a, 600b, e.g., includes the same antigen as the first binding element 604 or includes another antigen to which the attachment units 600a, 600b bind. One attachment unit 600b detaches from the first binding element 604, leaving a singleton, un-complexed indicator 602a. Indicator 602b is also visible in captured images as a singleton indicator. Based on a number of identified singletons and a number of identified complexes 606 (e.g., based on an overall ratio of identified singletons to identified complexes), a presence or level of the target chemical component can be identified. In some implementations, as in this example, a higher number of complexes, as compared to singletons, would correspond to a lower number of units 608 of the target chemical component, and vice-versa.

Figure 7A:
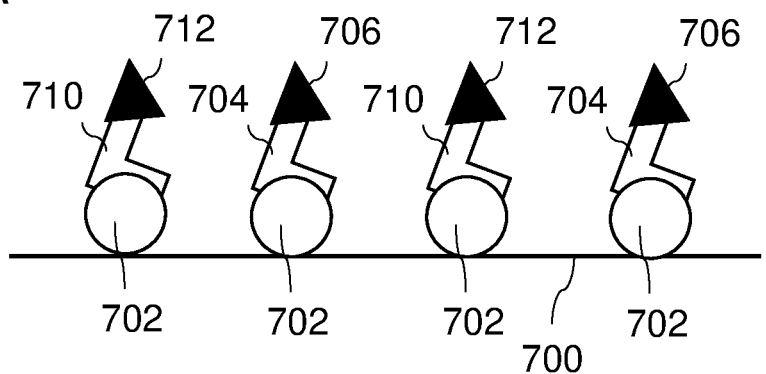
FIG. 7A is a schematic view of an example of surface-bound indicators.
Figure 7B:
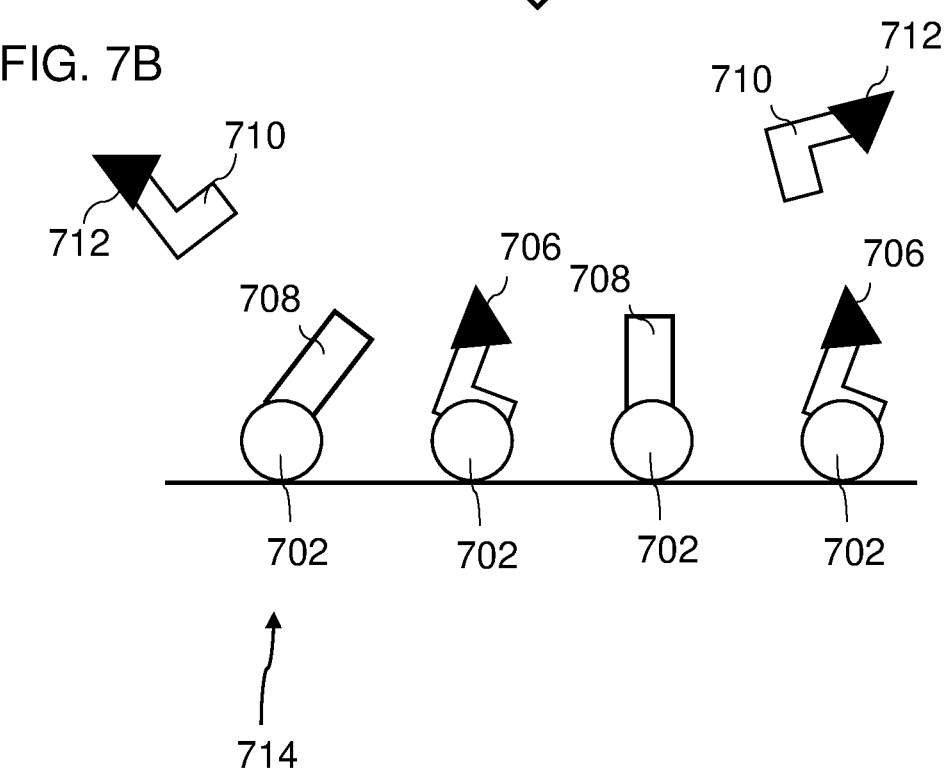
FIG. 7B is a schematic view of an example of a competitive assay of a sample.

In an example of competitive binding in a surface-bound detection mode for serology, as shown in FIG. 7A, antigens 702 are immobilized at known locations on a surface 700, as described throughout this disclosure. The antigens 702 are bound to detection antibodies 704, 710 that are bound to fluorescent indicators 706, 712. As shown in FIG. 7B, in the presence of sample antibodies 708 to the antigens 702 (the sample antibodies 708 being, in this example, the units of the target chemical component), at least some of the sample antibodies 708 displace detection antibodies and their corresponding indicators (e.g., detection antibodies 710 and indicators 712). In some implementations, mixing of the sample and/or formation of a thin layer of the sample, as described elsewhere in the disclosure, can cause the newly-detached detection antibodies 710 and indicators 712 to be ejected from an imaged portion of the sample. The sample antibodies 708 may be the same as or different from the detection antibodies 704.

Subsequently, an image of the sample is captured, and, based on a presence or lack of imaged indicators at the known locations at which the sample antibodies 708 are now attached (e.g., based on a number of such locations), a presence and/or a level of the sample antibodies 708 in the sample can be determined. For example, a lack of an indicator at location 714 indicates that a sample antibody 708 has become bound at that location, and therefore indicates that sample antibody 708 is present in the sample. A total number of such locations (e.g., compared to locations with indicators present) can be used to determine a concentration of the sample antibodies 708.

FIGS. 8A-8B show another embodiment of competitive surface-bound detection assaying. Antibodies 804, 814 are immobilized at known locations on a surface 800, as described throughout this disclosure. The antibodies 804, 814 are bound to antigens 802, 812 with other antibodies 808, 818. The other antibodies 808, 818 are bound to fluorescent indicators 806, 816. As shown in FIG. 8B, in the presence of sample antibodies 820 to the antigens 812 (the sample antibodies 820 being, in this example, the units of the target chemical component), at least some of the sample antibodies 820 displace detection antibodies and their corresponding indicators (e.g., antibodies 818 and indicators 816). A lack of a detected indicator 816 at location 822 indicates presence of sample antibodies 820 in the sample, as described in reference to FIG. 7B.

Competitive complexed-bead assays are not limited to immunoassays as in the example of FIGS. 6A-6B, and competitive surface-bound detection assays are not restricted to serology as in the example of FIGS. 7A-7B and 8A-8B. Rather, as described throughout this disclosure, appropriate selection of indicator type and attachment unit type can allow for many different types of assays to measure the presence or level of many different types of target chemical components. As described throughout this disclosure, attachment units and indicator types can be the same or different within multi-indicator complexes.

In some implementations, rather than units of the target chemical component competing for binding with pre-complexed or pre-surface-bound attachment units, the units of the target chemical component compete for initial binding with attachment units. For example, attachment units, indicators, and binding targets to which the attachment units may bind to form multi-indicator complexes may be solubilized into the sample when the sample, already containing units of the target chemical component, is placed in contact with a surface of an image sensor and/or a surface facing the surface of the image sensor, as described throughout this disclosure. The binding targets and the units of the target chemical component compete to bind with the attachment units, and a resulting final binding equilibrium is reflective of a concentration of the target chemical component in the sample.

The analysis processes and methods described herein (hereinafter referred to as "the processes"), including apparatus control functions (e.g., movement, illumination, and image capture instructions) and analysis functions (e.g., image analysis) can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers, e.g., as represented in FIG. 6. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit). Other embedded systems may be employed, such as NVidia® Jetson series or the like.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Processors or computer systems "configured" to perform one or more of the processes, algorithms, functions, and/or steps disclosed herein include one or more general or special purpose processors as described herein as well as one or more computer and/or machine-readable storage devices on which computer programs for performing the processes are stored.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

Components may be coupled (e.g., communicably coupled) over one or more networks or physically within a device. Coupling may include the capability to transmit data, including instructions, back and forth between the components.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML, page, to a user device, e.g., for purposes of displaying data to and receiving user input from a user interacting with the user device, which acts as a client. Data generated at the user device, e.g., a result of the user interaction, can be received from the user device at the server.

In operation, the computer system may cause sample illumination by a light source and/or image capture by the image sensor by transmission and reception of appropriate signals. For example, the computer system may send one or more signals to a light source to cause the light source to illuminate the sample; may send one or more signals to a mechanism associated with a lid to cause the lid to move with respect to a sensor surface; may send one or more signals to an image sensor to cause the image sensor to capture one or more images of a sample; and may receive, from the image sensor, signals representative of images captured by the image sensor.

Other implementations are also within the scope of the following claims.

The invention claimed is:
1. An apparatus comprising a surface configured to receive a sample
   an image sensor comprising an array of light sensitive elements,
   one or more processors, and
   one or more non-transitory, computer-readable media storing instructions that, when executed by the one or more processors, cause the one or more processors to perform operations comprising:
      capturing, by the image sensor, one or more images of the sample, wherein the sample comprises a plurality of first multi-indicator complexes, each first multi-indicator complex comprising
         a unit of a chemical component,
         an indicator of a first type attached to the unit of the chemical component, and
         an indicator of a second type attached to the unit of the chemical component,
         wherein the first type of indicator and the second type of indicator have different discernible characteristics, and
         wherein the array of light sensitive elements is disposed and structured to capture the one or more images based on received light from the indicator of the first type and the indicator of the second type;
      measuring, in a first image of the one or more images of the sample,
         a first proximity to one another of the respective indicator of the first type and the respective indicator of the second type in a first one of the first multi-indicator complexes, and
         a second proximity to one another of the respective indicator of the first type and the respective indicator of the second type in a second one of the first multi-indicator complexes;
      identifying, in the first image, the first one of the first multi-indicator complexes based on the first proximity, and the second one of the first multi-indicator complexes based on the second proximity;
      based at least in part on identifying the first one of the first multi-indicator complexes and the second one of the first multi-indicator complexes, generating a count of first multi-indicator complexes in the first image; and
      based on the count, identifying a presence or a level of the chemical component in the sample.

2. The apparatus of claim 1, wherein the indicator of the first type comprises a bead.

3. The apparatus of claim 1, wherein the indicator of the first type comprises a fluorescent label.

4. The apparatus of claim 1, wherein the indicator of the first type is attached to the unit of the chemical component by a first attachment unit, and wherein the indicator of the second type is attached to the unit of the chemical component by a second attachment unit.

5. The apparatus of claim 1, wherein identifying the presence or the level of the chemical component in the sample comprises:
   determining a first number of indicators of the first type that are included in the plurality of first multi-indicator complexes;
   determining a total number of indicators of the first type; and
   identifying the presence or the level based on the first number and the total number.

6. The apparatus of claim 1, wherein the array of light sensitive elements is within a near-field distance of the surface.

7. The apparatus of claim 1, wherein identifying the presence or the level of the chemical component comprises:
   determining a first number of indicators of the first type that are included in the plurality of first multi-indicator complexes;
   determining a second number of indicators of the first type that are excluded from the plurality of first multi-indicator complexes; and identifying the presence or the level based on the first number and the second number.

\* \* \* \* \*